United States Patent
Epstein et al.

(10) Patent No.: US 12,048,524 B2
(45) Date of Patent: *Jul. 30, 2024

(54) SURGICAL GUIDANCE SYSTEM WITH LOW INTERFERENCE METAL SUPPORT STRUCTURE

(71) Applicant: ACESSA HEALTH INC., Austin, TX (US)

(72) Inventors: Gordon Epstein, Austin, TX (US); Richard Spero, Austin, TX (US)

(73) Assignee: Acessa Health Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/134,435

(22) Filed: Apr. 13, 2023

(65) Prior Publication Data
US 2023/0248257 A1    Aug. 10, 2023

Related U.S. Application Data

(63) Continuation of application No. 17/510,253, filed on Oct. 25, 2021, now Pat. No. 11,653,852, which is a
(Continued)

(51) Int. Cl.
*A61B 5/06* (2006.01)
*A61B 5/00* (2006.01)
(Continued)

(52) U.S. Cl.
CPC .............. *A61B 5/062* (2013.01); *A61B 5/743* (2013.01); *A61B 8/4254* (2013.01); *A61B 34/20* (2016.02);
(Continued)

(58) Field of Classification Search
CPC .............................. A61B 5/704; A61B 5/6891
See application file for complete search history.

(56) References Cited

U.S. PATENT DOCUMENTS

| 6,618,612 B1 | 9/2003 | Acker et al. |
| 7,013,171 B2 | 3/2006 | Rhodes |

(Continued)

OTHER PUBLICATIONS

Notice of Allowance for U.S. Appl. No. 17/510,253 dated Jan. 25, 2023.
(Continued)

*Primary Examiner* — Rochelle D Turchen
(74) *Attorney, Agent, or Firm* — Vista IP Law Group, LLP (57) ABSTRACT

In accordance with the invention, a reliable apparatus for guiding an ablation probe to a target location inside a human body is thus provided. The apparatus allows incorporation of a conventional metal operating room table, but further comprises a substantially non-conductive separation structure positioned over the metal operating room table and underneath a horizontally oriented electromagnetic field generator. The resultant structure is adapted to support a human body in the prone or supine position over the operating table. Further support padding may also be provided. The electromagnetic field generator creates an electromagnetic field that extends through the torso of said human body positioned over the electromagnetic field generator. An ultrasound probe and ablation probe interacts with the electromagnetic field to generate positional information that is processed by a computing device to generate a graphic representation of location information on a display device.

11 Claims, 6 Drawing Sheets

Related U.S. Application Data continuation of application No. 14/872,507, filed on Oct. 1, 2015, now Pat. No. 11,160,469.

(60) Provisional application No. 62/059,856, filed on Oct. 4, 2014.

(51) Int. Cl.
| | | |
|---|---|---|
| *A61B 8/00* | (2006.01) | |
| *A61B 34/20* | (2016.01) | |
| *A61G 13/10* | (2006.01) | |
| *A61G 13/12* | (2006.01) | |
| *A61B 8/08* | (2006.01) | |
| *A61B 18/00* | (2006.01) | |
| *A61B 18/14* | (2006.01) | |

(52) U.S. Cl.
CPC ......... *A61G 13/10* (2013.01); *A61G 13/1285* (2013.01); *A61B 5/6891* (2013.01); *A61B 5/744* (2013.01); *A61B 8/0841* (2013.01); *A61B 2018/00577* (2013.01); *A61B 18/1482* (2013.01)

(56) References Cited

U.S. PATENT DOCUMENTS

| | | | |
|---|---|---|---|
| 9,538,991 B2 * | 1/2017 | Menon | ............... A61B 10/0233 |
| 2004/0199072 A1 | 10/2004 | Sprouse et al. | |
| 2005/0149013 A1 | 7/2005 | Lee | |
| 2005/0154282 A1 | 7/2005 | Li et al. | |
| 2005/0245821 A1 | 11/2005 | Govari et al. | |
| 2008/0186018 A1 | 8/2008 | Anderson | |
| 2009/0171203 A1 | 7/2009 | Avital et al. | |
| 2010/0210939 A1 | 8/2010 | Hartmann et al. | |

OTHER PUBLICATIONS

Ultrasound, National Institute of Biomedical Imaging and Bioengineering, Jul. 2013 (Year: 2013).
Final Office Action for U.S. Appl. No. 14/872,507 dated Apr. 16, 2021.
Final Office Action for U.S. Appl. No. 14/872,507 dated Apr. 16, 2020.
Final Office Action for U.S. Appl. No. 14/872,507 dated Feb. 20, 2019.
Non-Final Office Action for U.S. Appl. No. 14/872,507 dated Dec. 11, 2020.
Non-Final Office Action for U.S. Appl. No. 14/872,507 dated Sep. 13, 2019.
Non-Final Office Action for U.S. Appl. No. 14/872,507 dated Jul. 31, 2018.
Notice of Allowance for U.S. Appl. No. 14/872,507 dated Jul. 8, 2021.

* cited by examiner

Figure 8

SURGICAL GUIDANCE SYSTEM WITH LOW INTERFERENCE METAL SUPPORT STRUCTURE

CROSS REFERENCE TO RELATED APPLICATIONS

This application is a continuation of U.S. patent application Ser. No. 17/510,253, filed Oct. 25, 2021, which is a continuation of U.S. patent application Ser. No. 14/872,507, filed Oct. 1, 2015, now U.S. Pat. No. 11,160,469, which claims priority to U.S. Provisional Application Ser. No. 62/059,856, filed Oct. 4, 2014, both of which are hereby incorporated herein by reference in their entirety.

TECHNICAL FIELD

The invention relates to guiding surgical instruments during a procedure where the anatomical feature operated upon is not exposed to view and the patient is positioned in the supine or prone position.

STATEMENT REGARDING FEDERALLY SPONSORED RESEARCH OR DEVELOPMENT (Not applicable)

BACKGROUND OF THE INVENTION

Today, surgeons use various forms of imaging to make possible or assist in a wide range of surgical procedures. Imaging allows for more precise operations that reduce collateral damage and shorten recovery time as well as enhance survival rates.

Imaging systems may use a wide range of technologies. These imaging systems are of particular value in the performance of minimally invasive surgical procedures, where the desire to minimize damage to healthy tissue is promoted by minimizing the width of surgical instruments and introducing them into the body through elongated narrow diameter guidance and support members.

For example, surgical macerators may be supported at the end of a cable and sheath mechanical drive system where the cable and sheath serves the additional function of driving and guiding the macerator to the point where the surgery is to be performed. Such a macerator may include a fiber optic bundle with optics for imaging the vicinity of the tissues near the macerator and conveying that image to, for example, a display system with a n LCD display for presenting the images to the surgeon, allow him to quickly and reliably operate on the unwanted tissue.

Other approaches involve the introduction of the end of a fiber optic bundle with imaging optics into an existing body cavity or channel, and transmitting the image to the other end of the fiber optic bundle, where it may be received by focusing optics and an image sensor, such as a CCD transducer. Such devices may be of small caliber, for example, narrow enough to enter the nose and be introduced into the throat.

Still another possibility is to create a cavity in the body, for example by insufflating the abdominal cavity. One may then use the cavity as an imaging space allowing an optical camera to inform the surgeon with optically generated images of the position and orientation of the instrument and the anatomical feature being operated upon, thus allowing the surgeon to perform the surgery.

An different dimension of visualization may be achieved through the use of ultrasound imaging. For example, an ultrasound transducer may be positioned against the surface of an organ to generate an image of the interior of the organ. Such imaging may be used to show anatomical features inside the organ and the position of instruments, such as an ablation probe.

Such systems are of particular value during surgical procedures as they increase the amount of information available to the surgeon during a surgical procedure, such as the ablation of an undesired anatomical artifact, such as a uterine fibroid.

An alternate approach to imaging is the use of electromagnetic sensor systems to determine the position and orientation of surgical instruments. Such systems are typically employed in conjunction with such procedures as hand surgery. Generally, such systems employ electromagnetic position information components at the point of the instrument. The position information components are mechanically fixed to the surgical instrument. The position information components are coupled to an electromagnetic field generator. Typically the electromagnetic field generator comprises a flat planar member with electromagnetic antennae distributed relative to its surface. The antennae are electromagnetically coupled to the position information components, resulting in the generation of phase and amplitude information that is a function of the position and orientation of the position information components.

This information is processed by a computer associated with the system, for example a personal computer or other dedicated central processing unit, microprocessor, or the like. Information indicating the absolute position and orientation of the position information components and the surgical instrument may be generated in such systems. Because the position information components are fixed to the instrument, position and orientation information for the position information components can be transformed into position and orientation information for the surgical instrument.

In such systems, the computer may also be provided with a model of the shape of the instrument, for example a model generated by a computer aided design program. The model may be used by the computer to generate an image of the instrument, of a diagrammatic representation of operative aspects of the instrument. After processing the information from the electromagnetic field generator, the computer can thus produce representations of the instrument in space, which can be combined with anatomical image information from the ultrasound subsystem (or other imaging device or devices) to guide the surgeon.

Such an electromagnetic field generator is typically mounted vertically displaced upwardly above the top surface of the operating table, for example in connection with head and neck surgery, positioned above the table, and creating a field horizontally displaced from the generator (but closely adjacent thereto because of the relatively small dimension of the anatomy) in the head and neck. This allows the generation of an image, for example in the case of head surgery, corresponding to instrument position on a display field corresponding to a profile view of the head of the patient. In this respect, the electromagnetic field generator may be viewed as an analog of an x-ray plate of the type placed on one side of the head of the patient (for example the right side of the head of the patient) for receiving x-rays originating from the other side (for example the left side of the head of the patient).

SUMMARY OF THE INVENTION

While the performance of such systems has been recognized as a significant advance, looked at another way, such systems actually suffer from limitations intrinsic to their strength, that is being mounted on the side of a patient allowing easy access to the anatomy being operated upon. However, such arrangement will not work well to image the anatomy during a surgical procedure on an organ in the torso, for example the uterus, because of the width of the torso, which is substantially larger than the head or neck.

In accordance with the invention, it is proposed to have a patient lay on top of a flat horizontal electromagnetic field generator. Such an arrangement would also, in many cases, make possible more accurate and convenient imaging. However, initial attempts at placement of the electromagnetic field generator under the patient resulted in poor imaging. In accordance with the invention, there is provided a horizontal mounted electromagnetic field generator capable of generating high-quality images substantially on a par with those generated by side positioned field generators used in head and neck surgery, but for a support apparatus that could separate the field generator from the metal operating room table to prevent interference as well as support the weight of a patient while protecting the horizontal electromagnetic field generator from damage.

In the case of head and neck surgery, placement of a vertically mounted electromagnetic field generator having a length and a width commensurate with the anatomy related to a particular procedure is convenient because the thickness of the electro-magnetic field generator is relatively small. This allows space creating considerable freedom of movement for the surgeon.

As alluded to above, when operating on the torso, this is not a practical solution for several reasons. First, most operating tables are of relatively narrow dimension generally matching the width of the patient when the patient is positioned lying down with his back resting on the table. An electromagnetic field generator cannot fit on a conventional narrow operating table. Moreover, even if it could, the surgeon and personnel assisting in the procedure would not have close access to the patient. Another potential problem is that an imaging device placed on the side of the patient will block access to certain parts of the body, though this may be less of a problem with respect to procedures involving accessing the site of the operation from the top of the reclining patient.

There also exists the potential that greater distances, between the electromagnetic field generator and the anatomy involved in the procedure, may reduce the accuracy of the system. In the c will will ase of an electromagnetic field generator located, for example adjacent the left side of a patient in the supine position, such greater distances may be presented with respect to placement of instruments on the right side of the patient. Accordingly, in accordance with the invention, the electromagnetic field generator has been located in a plane substantially parallel to the plane of the operating table. However, while electromagnetic field generators operate properly when physician in a plane perpendicular to the operating table, mere relocation below a patient in the supine or prone position introduces errors into the system. In accordance with the invention, proper operation of the electromagnetic field generator is nevertheless achieved. Thus the invention provides significant advantages by removing limitations intrinsic to the electromagnetic field generator being placed on the side of a patient.

The option of placing a patient in the supine position over a flat horizontal electromagnetic field generator resting on the operating table, in many circumstances, presents advantages, including allowing for more accurate and convenient imaging, the absence of an obstruction in the operating area, eliminating the need for wider operating tables, and simplifying and minimizing the physical structures in the operating area, thus improving likelihood of maintaining a sterile field. At the same time, the inventive system provides the additional value of protecting the horizontal electromagnetic field generator from damage. The present invention thus fulfills existing needs in the field of medicine and provides substantial advantages.

While horizontally oriented electromagnetic field generators are known in connection with magnetic tracking systems such as those sold by Northern Digital Inc., of Waterloo, Ontario, such systems are known to be problematic, particularly in connection with stray electromagnetic fields, and the placement of various materials adjacent the electromagnetic field generator. These systems incorporate tabletop electromagnetic field generators, also referred to as tabletop field generators. Insofar as such systems are known to exhibit problems, manufacturers have sought to address this by the provision of barriers which have the object of reducing tracking distortions caused by conductive or ferromagnetic materials located below the electromagnetic field generator. Nevertheless, in practice, it has been discovered by the applicants that such systems nevertheless suffer from tracking problems when integrated into overall surgical systems.

In accordance with the invention, it has been discovered that reliability and error issues associated with horizontally positioned electromagnetic field generators, rather than owing their origins to consequences of the integration of the electromagnetic field generator into overall systems including ultrasound transducers and software processing of collective position data, appear not to involve software issues at the heart of the problem. Rather, inventors have discovered that unwanted system characteristics, appear to be the result of interactions with structural elements in the operating table, notwithstanding the provision of a barrier.

It is believed that these structural elements have electrical and/or ferromagnetic characteristics which degrade performance of the overall system. Accordingly, the invention contemplates isolation of the electromagnetic field generator from such structural elements. More particularly, in accordance with the preferred embodiment of the invention, a spatial isolation member is employed.

The use of the spatial isolation member also has the advantage of raising the operating field, which is advantageous in so far as the standard height of operating tables currently in use is the result of historical decisions made at a time when the average height of an individual was lower than today. Higher field height is thus more suited, on average, to today's surgeons, not only for a horizontally mounted electromagnetic field generator, but for a support apparatus that could separate the field generator from the metal operating room table to prevent interference as well as support the weight of a patient.

In accordance with the invention, an apparatus for guiding an ablation probe to a target location inside a human body is provided. The apparatus comprises a metal operating room table and a substantially non-conductive separation structure positioned over the metal operating room table. The apparatus comprises an electromagnetic field generator, which is located over the substantially non-conductive separation structure and adapted to support a human body. The electromagnetic field generated is positioned between the human body and the metal operating room table. The electromagnetic field generator creates an electromagnetic field that extends through, for example, the torso of the human body that has been positioned over the electromagnetic field generator. The apparatus comprises an ultrasound probe that interacts with the aforementioned electromagnetic field to generate ultrasound probe positional information. The ultrasound probe is adapted to generate an ultrasound image of a region having a known spatial relationship to the probe.

The apparatus comprises an ablation probe that interacts with the electromagnetic field to generate ablation probe positional information. A computing device is responsive to the ultrasound probe positional information. The ablation probe positional information generates a graphic representation showing the positional relationship between the ultrasound image and the ablation probe to guide placement of the ablation probe into an anatomical location imaged by the ultrasound probe. The apparatus additionally comprises a display device responsive to the computing device so as to display a graphic representation.

In accordance with the invention, the display may comprise a guidance animation displayed on the display device, which is generated by the computing device, which processes the guidance information. Real-time correctional information can be viewed by a user in the guidance animation.

The substantially non-conductive separation structure may be a foam rubber or foam plastic member and may be formed integrally with the electromagnetic field generator.

The electromagnetic field generator may be in the form of a planar member having dimensions that are roughly commensurate with the area of the body to be imaged.

The apparatus may comprise a cushioned layer disposed over said electromagnetic field generator and it may comprise a nonconductive protective member disposed over the electromagnetic field generator and cushioning disposed over the nonconductive protective member.

The apparatus may comprise adjustable features including but not limited to, a removable section or sections, for example, underneath the head, the feet, and/or the legs of the human body.

The orientation of the electromagnetic field generator may generally align with a plane that is roughly parallel to the ground and oriented above and parallel to the plane defined by the surface of the operating room table.

BRIEF DESCRIPTION THE DRAWINGS

The operation of the invention will become apparent from the following description taken in conjunction with the drawings, in which.

DETAILED DESCRIPTION OF THE PREFERRED EMBODIMENTS

Figure 1:
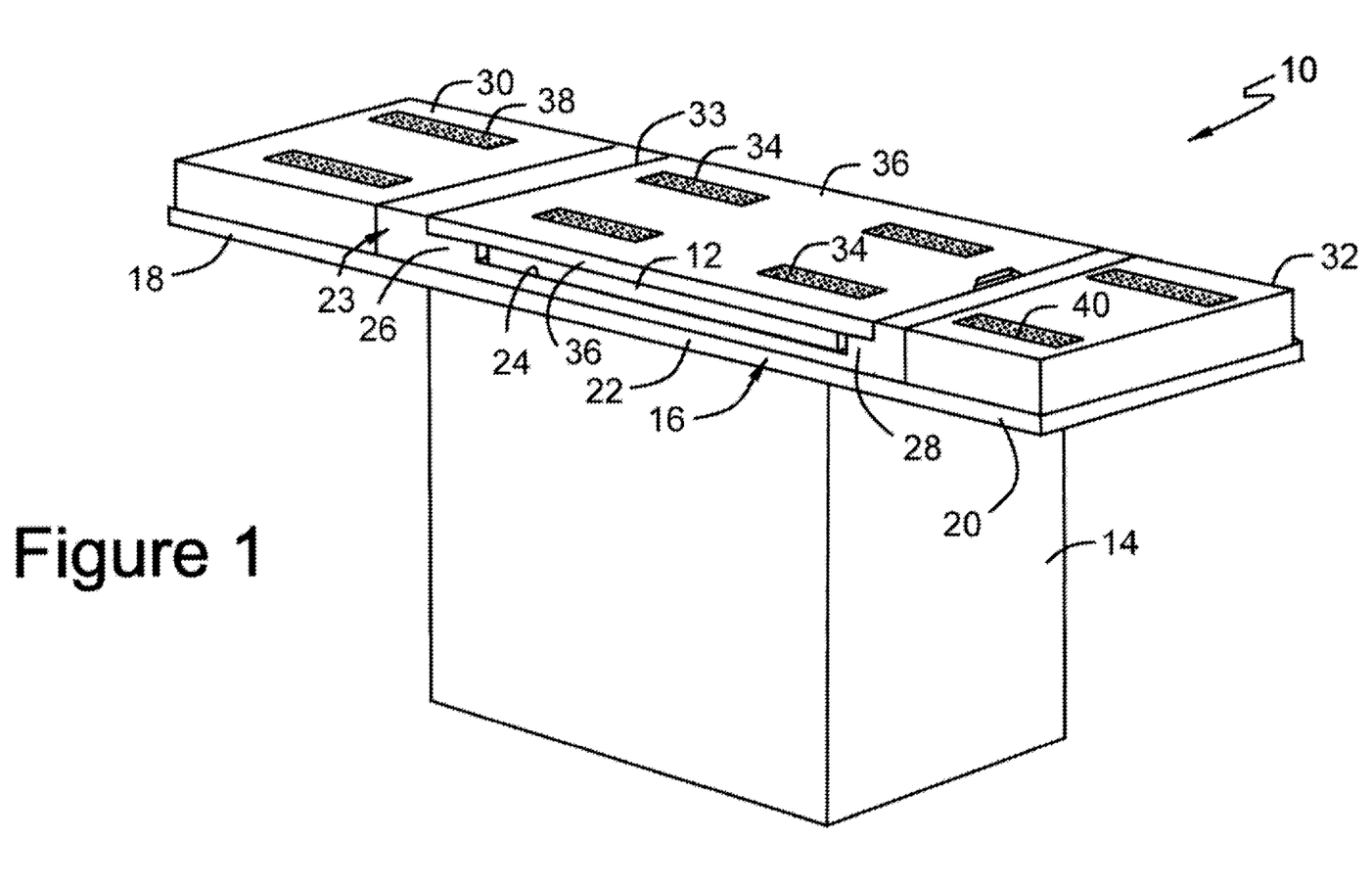
FIG. 1 is an isometric view of the inventive operating room tabletop field generator housing assembly as a part of an operating room table.
Figure 2:
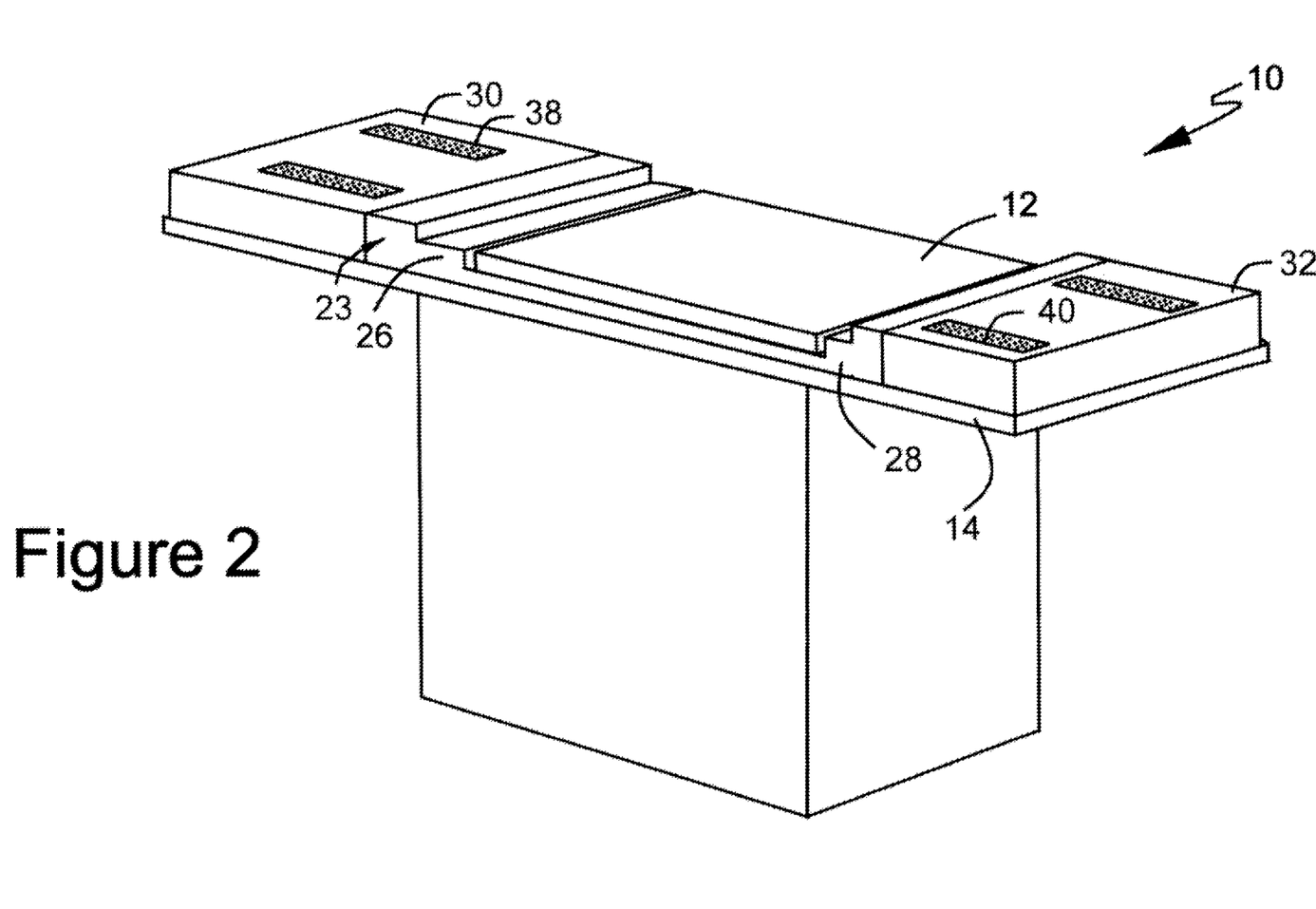
FIG. 2 is an isometric view similar to the view of FIG. 1, but with the top face member removed for clarity of illustration, exposing internal components of the inventive system.

Referring to FIGS. 1-4, with particular attention to FIG. 1, the inventive operating room table, which is particularly adapted for housing an electromagnetic field generator in a unitary assembly, may be understood. The operating room table assembly 10, which functions to house a tabletop electromagnetic field generator 12, has the overall shape, when assembled, of a rectangular solid as seen in FIG. 2. It may be supported on any suitable support, such as the platform formed by rectangular solid 14, as illustrated, or four table legs adapted to roll, for example, into and out of an operating room. Electromagnetic field generator 12 may be any commercial device in this class, including the Aurora system manufactured by Northern Digital Inc.

Table assembly 10 comprises an operating table of, for example, conventional design. This may be a steel carriage with wheels or rectangular base support 14, supporting a platform member 16. Platform member 16 comprises a leg supporting portion 18 and a head supporting portion 20.

In accordance with the preferred embodiment, platform member 16 is made of a rigid strong construction capable of supporting the human body and with a rigidity which enables leg supporting portion 18 to support the outstretched legs of an individual. In accordance with the construction of operating tables of the type which are commonly on the market, platform member 16 may be made of steel, for example steel supporting members having, for example, the configuration of cylindrical tubes, rectangular tubes, elongated orthogonal members joined along their length forming an L-beam, I-beam construction and so forth. If desired, leg supporting portion 18 and head supporting portion 20 may be made to rotate on a hinge, allowing them to rest hanging down in the vertical position. This allows the operating room table to take up minimal space when not in use. At the same time, means may be provided for such hinging leg and head supporting portions 18 and 20 to be locked in the horizontal position (as illustrated) to support the head and legs.

In accordance with the invention, it is contemplated that support 14 and platform member 16 may together comprise a conventional operating room table. More particularly, it is one of the objects of the present invention to provide support structure to be used with a conventional operating table to enable use of an electromagnetic field generator while still preventing inaccuracies or other unreliability in the readings from the system associated with the electromagnetic field generator.

Figure 3:
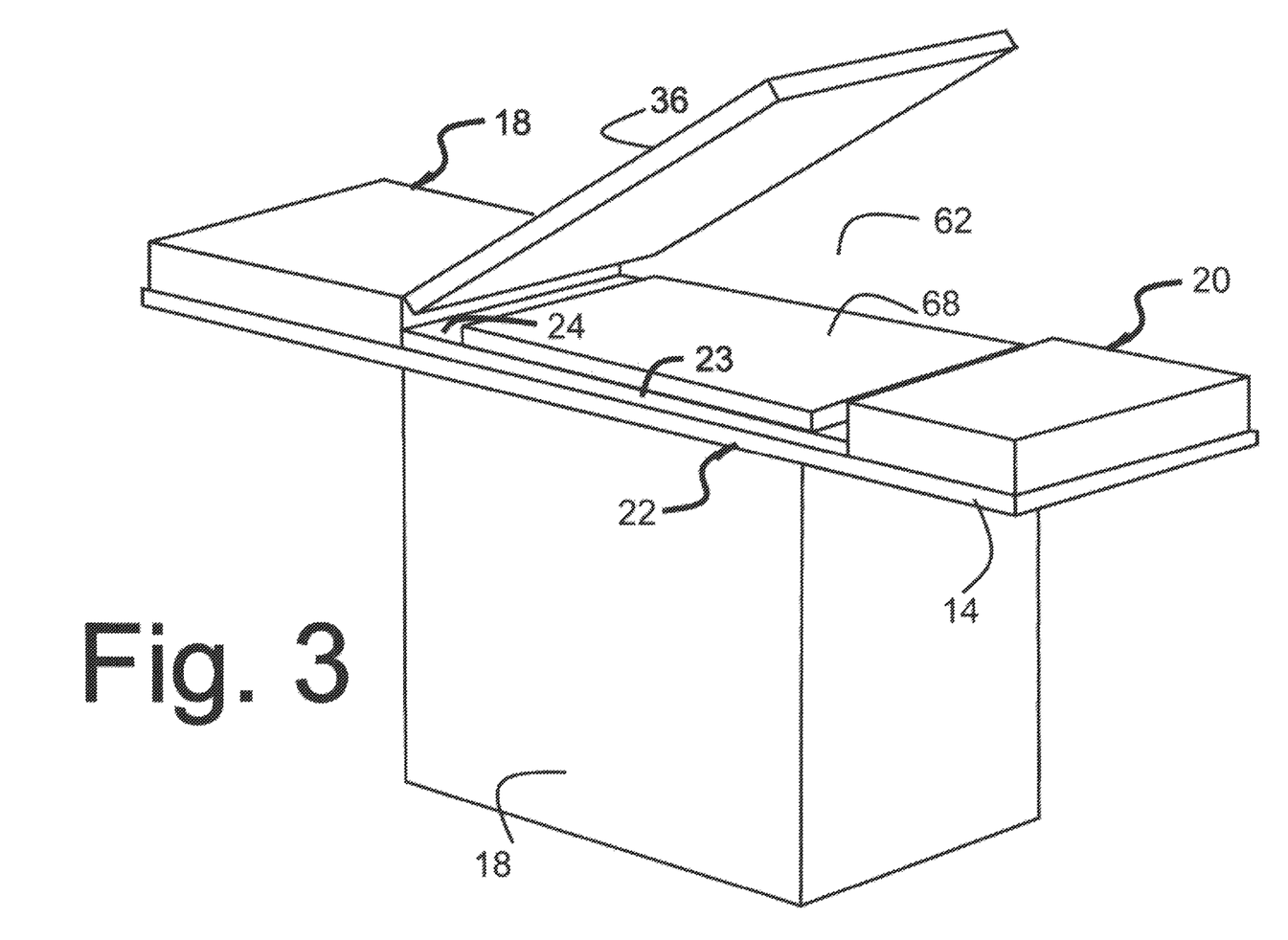
FIG. 3 is an isometric view similar to that of FIG. 1 showing the top face member hinged open to allow placement of an electromagnetic field generator.
Figure 4:
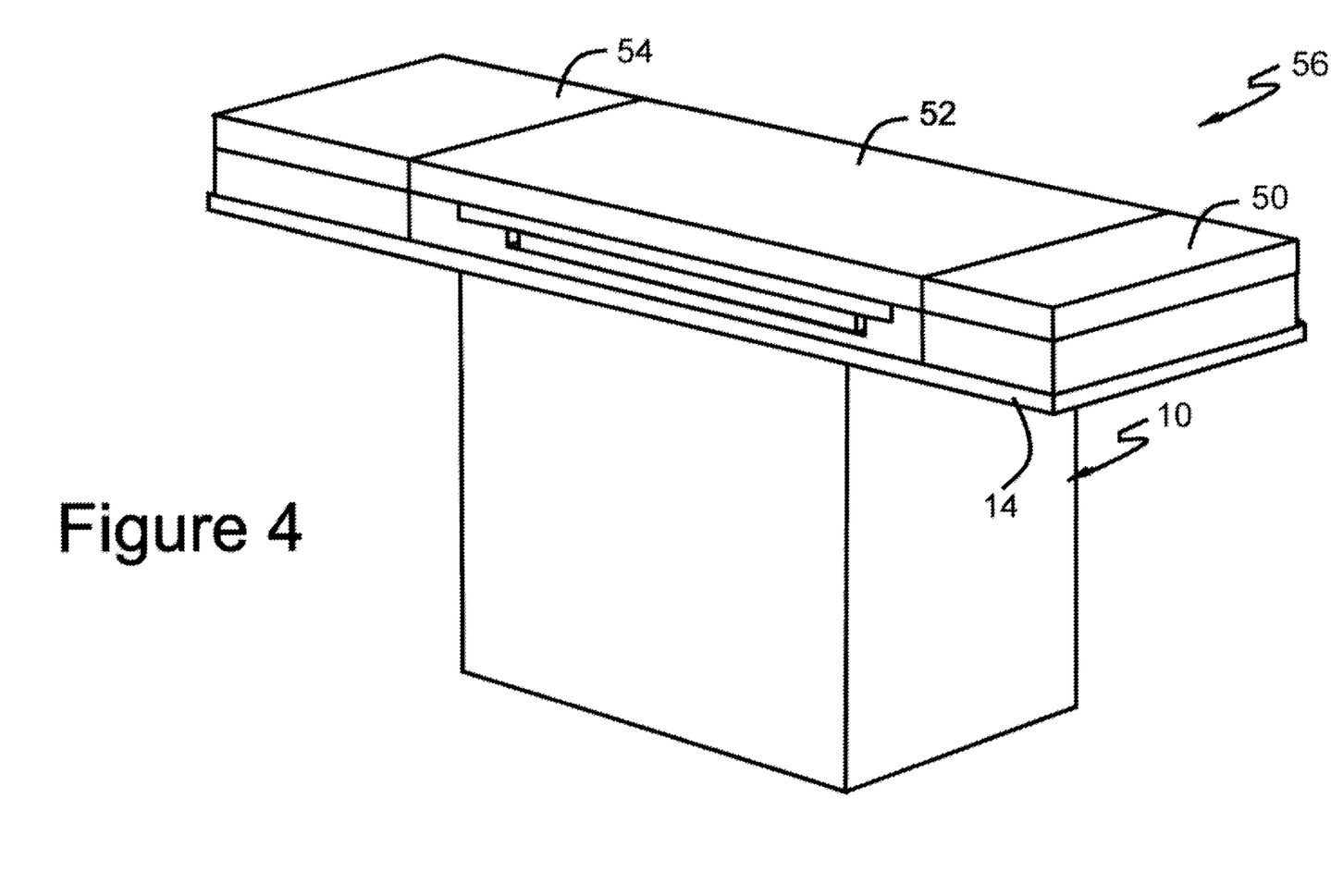
FIG. 4 is an isometric view including the top cushions of the inventive table system and forming a completed assembly.
Figure 5:
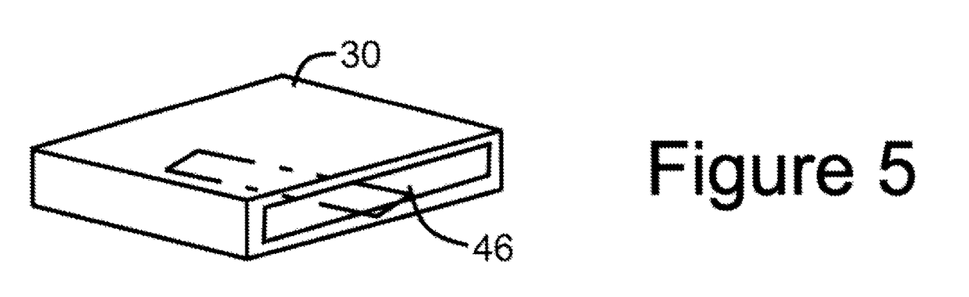
FIGS. 5-7 illustrate components of the inventive system.
Figure 6:
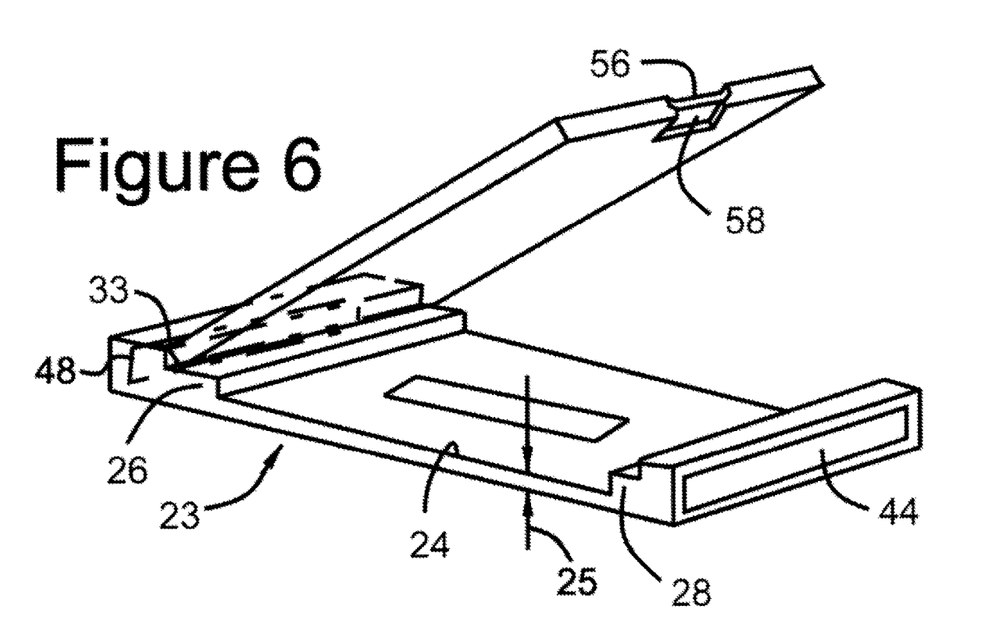
Figure 7:
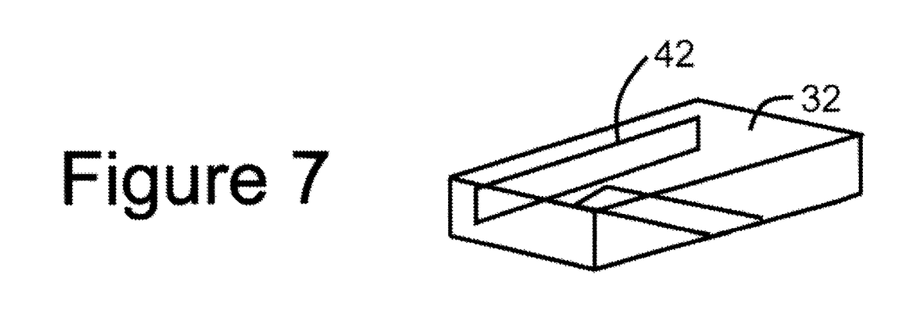

The torso of the patient is supported by central portion 22. Referring to FIGS. 1 and 3, central portion 22 is designed to support electromagnetic field generator 12. Referring to FIGS. 5-7, central portion 22 supports a central support member 23. Central support member 23 includes a well 24 which is configured to receive electromagnetic field generator 12. The portion of central support member 23 which supports electromagnetic field generator 12 has a thickness 25 greater than ¼ inch, preferably greater than ½ inch and most preferably greater than three-quarters of an inch, although this thickness will vary depending on the characteristic of the electromagnetic field generator and other associated system components. A pair of steps 26 and 28 (FIG. 2) define the lengthwise limits of well 24, and have a height which substantially matches the thickness of electromagnetic field generator 12.

A head support member 32 is positioned on one side of central support member 23 to provide support for the head of the patient. This allows central support member 23 to lie flat across steps 26 and 28, and electromagnetic field generator 12. As shown in FIG. 3, such placement may be facilitated by an optional hinge 33, which joins the main body portion of central support member 23 and top face member 36. Hinge 33 may be made of vinyl-coated fabric or any suitable material. A leg support member 30 is positioned on the opposite side of central support member 23 to provide comfortable support for the legs of the patient.

In accordance with the invention, it is contemplated that support members 23, 30 and 32 will be made of relatively rigid material, such as a rigid foam plastic. Alternatively, foam plastic with relatively little flexibility, for example high density foam rubber may be used. However, lighter materials are preferred because they are easier to handle. In accordance with the invention, support members 23,30 and 32 are covered with a suitable outer covering, such as vinyl or other plastic material.
While a textile may be used, a plastic covering is preferred because of the ease with which the same may be cleaned and because it serves as a barrier which prevents contamination of the internal support core members forming support members 23, 30 and 32.

In accordance with a preferred embodiment of the invention, it is contemplated that a set of cushions will be put over support members 23, 30 and 32. Such cushions are secured to their respective support members by mating strips of Velcro® hook and loop adhesion fabric which are adhered to the facing sides of the support members and their respective cushions. More particularly, adhesion fabric strips 34 are secured to the top face 36 of central support member 23. Similarly, adhesion fabric strips 40 and 38 are secured to head and leg support members 32 and 30, respectively.

In similar fashion, head support member 32 is secured to central support member 23 by adhesion fabric 42 on head support member 32 and adhesion fabric 44 on central support member 23. Leg support member 30 is secured to central support member 23 by adhesion fabric 46 on leg support member 30 and adhesion fabric 48 on central support member 23. Likewise, the rigidity and stability of the structure may be insured by including mating adhesion fabric strips at all interfaces between support members and other support members, cushions and other cushions and interfaces between cushions and support members.

More particularly, the inventive table assembly 10 may include a head cushion 50, a central cushion 52 and a leg cushion 54, thus completing the structure of the inventive operating table 56. Head cushion 50, central cushion 52 and leg cushion 54 may be made of any suitable cushioning material, such as flexible foam rubber, flexible foam plastic or any other material suitable for cushioning, bedding or other flexible support. In accordance with the invention, it is contemplated that head cushion 50, central cushion 52 and leg cushion 54 will be made of a more flexible, softer material then central, head and leg support members 23, 32 and 30. The requirement for cushions 50-54 is of a soft feeling cushioning member. On the other hand the requirements for central, leg and head support members 23, 30 and 32 are for no or low flexibility as their primary function is to support electromagnetic field generator 12 in a desired position.

As alluded to above, when it is desired to use the inventive system, support members 23,30 and 32 are placed on a conventional operating table, with the various elements optionally but preferably held together by Velcro® type joining members. Next, top face member 36 is hinged upwardly to the position shown in FIG. 3, by putting the fingers through cutout 56 and pulling upwardly against indentation 58 (FIG. 6). Electromagnetic field generator 12 is then placed in position as illustrated. Top face member 36 is hinged downwardly over electromagnetic field generator 12 to the position illustrated in FIG. 1. The assembly is then ready to receive the head cushion 50, central cushion 52 and leg cushion 54 which are secured in place by Velcro® type joining members, as detailed above. The system then takes the configuration shown in FIG. 4, and is ready to receive patient 60 as illustrated in FIG. 8.

Figure 8:
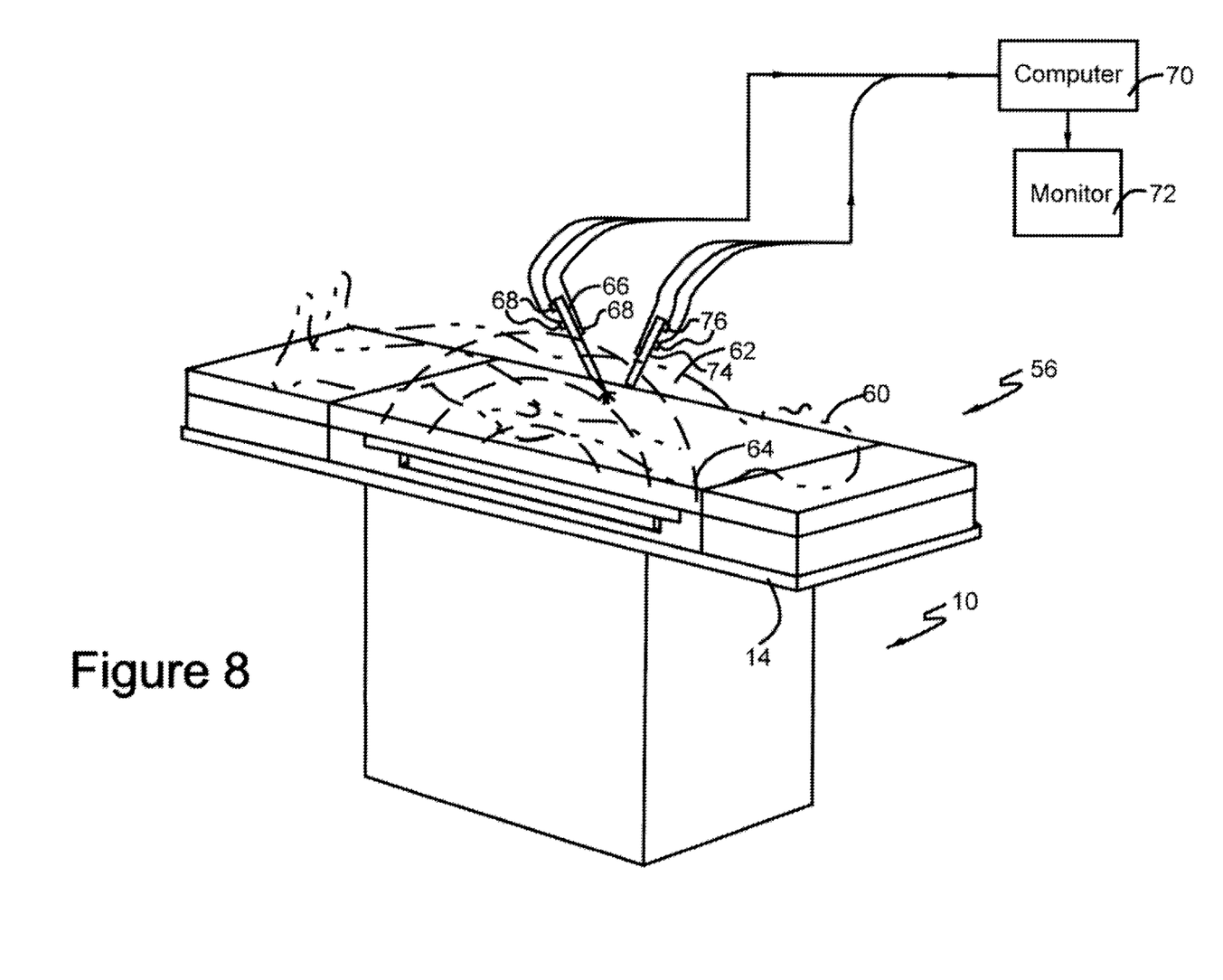
FIG. 8 is an isometric view illustrating the system of the invention In use.

Referring to FIG. 8, the operation of the inventive operating room patient supporting table housing an electromagnetic field generator housing assembly 10 may be understood. A patient 60 may be positioned in the supine position lying on the operating room table above the electromagnetic field generator 12 such that the torso 62 of patient 60 is positioned directly above the horizontal field generator 12. When turned on, the horizontal field generator 12 produces an electromagnetic field 64 which is used in the generation of position and orientation information in three dimensions. A probe 66, for example an ablation probe 66, is inserted into, for example, the insufflated abdominal cavity of patient 60. Probe 66 carries a number of position information components, for example position detectors 68, which may be coupled to a computer 70. Computer 70 produces an image of a target location, an image of the physiology (for example, a physiological image generated by an ultrasound probe 74, where ultrasound probe position and orientation is detected by detectors 76) an image of probe 66 on monitor 72 together with an image of the physiology. A transducer 68, which may be mounted on or contained within probe 66 interacts with horizontal field generator 12, through electromagnetic field 64, generates signals corresponding to a set of positional information coupled to computer 70. The positional information is interpreted by a computer 70 which then displays images of probe 66 (or optionally an avatar representing the state of a critical functionality) and positional information on the physiological structure of interest on monitor 72.

Thus, computer 70 combines the ultrasound probe positional information with the ablation probe positional information to generate an image which can be combined with a target avatar, to create a guidance animation which may be displayed in addition to and/or instead of image info nation on computer monitor 72. In accordance with the invention, guidance system animation and/or images are viewed by the surgeon during a procedure, for the purpose of assisting with the manipulation of ablation probe 66 and ultrasound probe 74.

After an operation has been completed, the various components of the operating table may be removed and stored separately, and the operating table used in a conventional fashion until the inventive system is again required or desired.

Modifications of the particular structures disclosed are within the intended scope of the invention. The compartment forming support members 23,30 and 32 may be made from foam material as disclosed above in accordance with a preferred embodiment, or alternatively, plastic, wood, or a non-conductive composite material.

While illustrative embodiments of the invention have been described, it is noted that various modifications will be apparent to those of ordinary skill in the art in view of the above description and drawings. Such modifications are within the scope of the invention which is limited and defined only by the following claims.

What is claimed:

1. A patient positioning device, the positioning device comprising:
 a non-conductive separation structure positionable on an operating room table, wherein the non-conductive separation structure comprises a base having a recess, and a cover member moveable relative to the base, wherein the cover member is configured to cover the recess of the base when the cover member is in a closed position, and wherein the recess of the base is exposed when the cover member is in an open position;
 wherein the recess of the base of the non-conductive separation structure is configured to accommodate an electromagnetic field generator, and wherein the non-conductive separation structure is configured to support a human body when disposed between the human body and the operating room table.

2. The positioning device of claim 1, wherein the non-conductive separation structure comprises a foam rubber material.

3. The positioning device of claim 1, wherein the non-conductive separation structure is formed integrally with the electromagnetic field generator.

4. The positioning device of claim 1, wherein the non-conductive separation structure has a thickness in a range between 0.25 inches and 7.0 inches.

5. The positioning device of claim 1, wherein the non-conductive separation structure has a thickness in a range between 0.50 inches and 7.0 inches.

6. The positioning device of claim 1, further comprising cushioning disposed over the non-conductive separation structure.

7. The positioning device of claim 1, further comprising one or more removable features selected from the group consisting of
 a section configured to support a head of the human body;
 a section configured to support feet of the human body; and
 a section configured to support legs of the human body.

8. The positioning device of claim 1, wherein the electromagnetic field generator is orientated above and parallel to a plane defined by a surface of the operating room table.

9. The positioning device of claim 1, wherein the non-conductive support structure is configured to minimize electromagnetic interference between the electromagnetic field generator and the operating room table.

10. The positioning device of claim 1, wherein the non-conductive support structure is configured to reduce electromagnetic interference between the electromagnetic field generator and imaging equipment.

11. The positioning device of claim 1, wherein the non-conductive support structure fully encloses the electromagnetic field generator when the cover is in the closed position.

* * * * *